United States Patent [19]

Enscore et al.

[11] Patent Number: 4,559,222

[45] Date of Patent: Dec. 17, 1985

[54] MATRIX COMPOSITION FOR TRANSDERMAL THERAPEUTIC SYSTEM

[75] Inventors: David J. Enscore, Sunnyvale, Calif.; Robert M. Gale, Los Altos, Calif.

[73] Assignee: ALZA Corporation, Palo Alto, Calif.

[21] Appl. No.: 491,490

[22] Filed: May 4, 1983

[51] Int. Cl.$^4$ .................. A61F 13/00; A61L 15/03; A61K 9/70; A61K 31/745

[52] U.S. Cl. ........................ 424/28; 424/22; 424/83; 514/770

[58] Field of Search ............... 424/22, 28, 83, 357

[56] References Cited

U.S. PATENT DOCUMENTS

| | | | |
|---|---|---|---|
| 2,627,938 | 2/1953 | Frohmader et al. | 424/363 |
| 2,628,205 | 2/1953 | Shoemaker | 424/83 |
| 2,775,561 | 12/1956 | Frohmader | 424/358 |
| 3,029,188 | 4/1962 | Cyr et al. | 424/83 |
| 3,079,299 | 2/1963 | Heilig | 424/83 |
| 3,215,599 | 11/1965 | Thau et al. | 424/83 |
| 3,250,680 | 5/1966 | Menkart et al. | 424/357 |
| 3,293,205 | 12/1966 | Doyle et al. | 424/357 |
| 3,400,197 | 9/1968 | Lippmann | 424/357 |
| 3,574,827 | 4/1971 | Beerbower | 424/83 |
| 3,733,403 | 5/1973 | Chen | 424/83 |

FOREIGN PATENT DOCUMENTS 2021950 12/1979 United Kingdom ................ 424/28

*Primary Examiner*—Shep K. Rose
*Attorney, Agent, or Firm*—Steven F. Stone; Paul L. Sabatine; Edward L. Mandell

[57] ABSTRACT

Mineral oil (MO) polyisobutylene (PIB), colloidal silicon dioxide (CSD) mixtures suitable for use as drug containing matrices in transdermal delivery systems are disclosed. Preferred systems for dispensing moderately mineral oil soluble drugs contain at least about 6% CSD, have a MO/PIB of at least 1.0 and a viscosity of at least $1.5 \times 10^7$ poises. Preferred systems for dispensing clonidine have a clonidine permeability of at least $1.0 \times 10^{-4}$ µg/cm sec and a MO/PIB of at least 1.2.

18 Claims, 5 Drawing Figures

MATRIX COMPOSITION FOR TRANSDERMAL THERAPEUTIC SYSTEM

FIELD OF THE INVENTION

This invention relates to devices for delivering drugs and other active agents to the body and more particularly to a matrix composition having the characteristics of permeability, viscosity and adhesion desired for transdermal drug delivery systems.

BACKGROUND OF THE INVENTION

Various types of systems are known to the art for delivering biologically active agents (hereinafter "drugs") to the skin. These devices range from simple drug loaded creams, ointments and gels which are applied directly to the skin such as a nitroglycerin ointment for the treatment of angina, to more precisely controllable systems in which a drug is dispersed through a matrix of fixed configuration such as is shown in U.S. Pat. No. 3,923,939 to even more sophisticated systems which employ rate controlling membranes or other structures to precisely meter the quantity of drug that is administered through the skin for a prolonged period of time such as disclosed in U.S. Pat. Nos. 4,031,894 and 4,201,211, for example, all of which patents are incorporated herein by reference. Regardless of the actual structure of any particular system, all these systems utilize some form of a reservoir for the drug in which the drug to be dispensed is dispersed and this reservoir must have certain characteristics of viscosity, permeability, and adherence in order to render it suitable for use in a delivery system. This is particularly important in laminated systems without sealed edges such as described in the latter two patents, where the adhesive and reservoir layers must be viscous enough to prevent oozing of the layers. The latter two patents disclose mineral oil-polyisobutylene (MO-PIB) matrices for use in dispensing clonidine and scopolamine and such matrices are also useful for dispensing to the skin any moderately mineral oil soluble drug. Particularly suitable are those drugs whose solubility in mineral oil does not exceed approximately 5 mg/ml such as, in addition to clonidine and scopolamine; estradiol, phenylpropanolamine, propranolol, ouabain, salbutamol, guanabenz, labetolol, atropine, haloperidol, bromocryptine, chloropheniramine, metrifonate, isosorbide dinitrate, and nitroglycerin, for example.

In addition to the primary drug or drugs, the compositions may also contain other materials such as permeation enhancers to improve skin permeability, cytoprotective agents to reduce skin irritation, buffers to adjust pH and other materials all as is known to the art.

As disclosed in the latter two identified patents, a typical MO-PIB matrix composition will comprise a mineral oil of about 5 to 100 cp viscosity at 25° C. admixed with a blend of PIBs. The MO usually constitutes between 35%–35% by weight of the mixture and the PIB can also constitute between 35%–65% of the mixture. Th PIB blend usually comprises a low molecular weight (LMW) PIB (35,000–50,000 viscosity average molecular weight) and a high molecular weight (HMW) PIB, (1,000,000 to 1,500,000 viscosity average molecular weight). Preferred mixtures comprise 35%–65% mineral oil, 10–40% LMW PIB and 10–40% HMW PIB. The precise formulation of any reservoir composition is generally adjusted to try to provide a particular combination of characteristics such as viscosity, drug permeability and adhesion as required to meet the design requirements of the end product. In general, the PIB functions as a thickener and the MO as the solvent for the drug. Thus increasing the MO/PIB ratio generally increases permeability and descreases viscosity while decreasing the MO/PIB ratio has the opposite effects. It should also be noted, as disclosed in the latter two patents, that the same general MO-PIB mixtures can be tailored to be used either as a drug reservoir or as a contact adhesive for attaching the device to the skin and the adhesive may or may not contain an amount of drug material to provide a priming dose.

Typically, the drug to be dispensed is dissolved and dispersed throughout the matrix material in amounts higher than saturation such that the reservoir contains both a dissolved and dispersed phase. The dispersed phase is normally present in amounts sufficient to maintain the concentration of the drug in matrix at or above saturation during the intended dispensing life of the device. While amounts as high as 40% by weight of drug can be included, normally a matrix for use as a drug reservoir would contain up to about 20% by weight of drug and when used as the adhesive, with a priming dose, up to about 10% by weight of drug.

In attempting to optimize matrix compositions, we have determined that the compositions should have a viscosity of no less than about $1.5 \times 10^7$ poise and a sufficiently high permeability, $DC_s$, for the drug to be delivered to permit adequate release rates with reasonable size skin patches. With this combination of characteristics the drug delivery systems would have excellent physical characteristics in that they would retain their structural integrity, not ooze or flow, be readily removed from the package in which they are contained, be reasonably sized and, for the laminated systems, have a sufficiently high permeability to permit the rate controlling membranes to be the predominant means for controlling the rate of drug release from the system.

It was known that the viscosity of the matrix composition could be modified by varying the MO/PIB ratio. However, increasing the viscosity by increasing the proportion of PIB results in a decrease in the permeability of the system to undesirably low levels. Correspondingly, increasing the mineral oil content to raise permeability, yields low viscosity compositions which tended to cold flow and have poor structural characteristics. Prior to our invention, for example, an MO/PIB ratio of about 1.0 was the highest feasible level for use in commercially marketable transdermal systems.

Colloidal silicon dioxide (CSD) such as Cab-O-Sil ® manufactured by the Cabot Corporation and other similar colloidal silica materials are known thickeners for mineral oil (see for example, Cab-O-Sil ® Properties and Functions, Cabot Corporation, 125 High St., Boston, MA 02110). It was also known by others to use CSD to thicken other types of drug matrices such as disclosed in copending, coassigned U.S. Patent Application of Gale, et al. for Novel Bandage for Administering Beneficial Drug, Ser. No. 278,364, filed Jan. 29, 1981. In addition, CSD is approved by the FDA as a material generally recognized as safe for inclusion in topical pharmaceutical preparations.

Accordingly, it was decided to use CSD to increase the viscosity of MO-PIB matrix compositions. When amounts of CSD were added to certain MO-PIB compositions, it was unexpectedly found that the viscosity could be increased without decreasing the permeability and, in fact, within certain composition ranges of the various components of the matrix composition mixture, it was possible to produce MO-PIB compositions having not only increased viscosities but also increased drug permeabilities as well. Further within certain ranges, unexpected improvements in other properties of transdermal therapeutic systems using these compositions were obtained.

Thus in the prior art systems the mechanical and diffusional properties of the system were not independently variable (i.e., an increase in permeability invariably led to a decrease in the system viscosity, and vice versa). According to our invention, however, the use of CSD in certain formulations permits these properties to be independently variable and high permeability and high viscosity are both obtainable.

It is accordingly an object of this invention to provide a matrix composition for a drug delivery system having improved properties.

It is another object of this invention to provide matrix compositions having both high viscosities and high drug permeabilities.

It is another object of this invention to provide a drug loaded MO-PIB composition having a viscosity of at least $1.5 \times 10^7$ poise.

It is another object of this invention to provide a drug loaded matrix formed from mineral oil, PIB, CSD and a moderately mineral oil-soluble drug composition dispersed therethrough at a concentration above saturation.

It is another object of this invention to provide a rate controlled transdermal therapeutic system having a MO-PIB matrix with desired properties of viscosity, permeability and adhesion.

These and other objects of the invention will be readily apparent from the following description of the invention with reference to the accompanying drawings in which:

DESCRIPTION OF THE INVENTION

According to this invention, we have discovered that it is possible to fabricate MO-PIB matrix compositions having viscosities above $1.5 \times 10^7$ poise and high permeabilities for moderately mineral oil soluble drug compositions. As used herein, a moderately mineral oil soluble drug is a drug whose solubility in mineral oil is at least 10 μg/ml and no greater than approximately 5 mg/ml. Non-limiting examples of such drugs are, scopolamine, clonidine, estradiol, phenylpropanolamine, propranolol, ouabain, salbutamol, guanabenz, labetolol, atropine, haloperidol, bromocryptine, chlorpheniramine, metrifonate, isosorbidedinitrate, and nitroglycerin, for example. These viscosity and permeability characteristics can be obtained if the MO/PIB ratio is greater than about 1.0 and preferably in the range of 1.4–1.8 and the composition contains at least 5% and preferably 7.5% to 10% colloidal silicon dioxide (CSD). Such matrix compositions are capable of being loaded with up to about 40% by weight of moderately mineral oil-soluble drug compositions. In practice, however, when used as a drug reservoir, the loadings rarely exceed 20% and when used as an adhesive, rarely exceed 10%.

Figure 1:
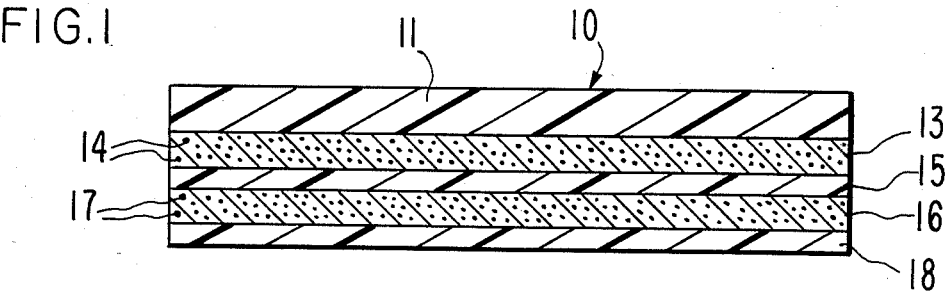
FIG. 1 is a schematic sectional view through a laminated transdermal therapeutic system.

Referring now to FIG. 1, a typical transdermal delivery system according to this invention would comprise a bandage 10 preferably formed from an impermeable backing 11, a reservoir layer 13 formed of a matrix material having drug 14 dispersed therethrough at a concentration greater than saturation, a drug release rate controlling layer 15 such as a permeable or microporous membrane through which drug may diffuse at a known rate, an adhesive layer 16 which may also contain a loading of drug 17 and a protective strippable coating 18. The various layers are laminated or otherwise assembled into a bandage having a predetermined size and shape all as known to the art. FIG. 1 describes a preferred embodiment but it should be recognized that one or more of the layers may be deleted or repeated, the basic transdermal system being a drug containing matrix provided with means for maintaining the matrix in drug transferring relationship with the skin.

In the following examples, adhesives and reservoirs having matrix compositions according to this invention are compared to the prior art control samples. In all the following examples, the MO and PIB were initially mixed together under ambient conditions to form a gel. Thereafter the drug composition and CSD (Cab-O-Sil ® M-5 and M-7), if any, were added with mixing to provide a uniform dispersion. The sample transdermal therapeutic systems 1.78 cm in diameter (area, 2.5 cm$^2$) made from such compositions were fabricated having reservoir layers approximately 50 μm thick, contact adhesive layers approximately 50 μm thick and rate controlling membranes of 25 micron thick microporous polypropylene membrane (commercially available under the trademark Celgard ® 2400) saturated with MO (0.9 mg MO/cm$^2$) all laminated together with an impermeable backing and a strippable liner as described in U.S. Pat. Nos. 4,031,894 and 4,201,211. In some cases where the adhesive composition adhered too strongly to the release liner, a 5–10 micron thick prime coat of 53% PIB/47% MO was applied between the adhesive and the liner. The MO used was a light mineral oil having a viscosity of 7 CP at 25° C., the LMW PIB had an average molecular weight of about 35,000 and the HMW PIB had an average molecular weight at about 1,200,000.

It should be noted that in the following examples, the compositions of the adhesive and reservoir matrices are the compositions used in the fabrication of the delivery system. Since the MO/PIB ratio for the adhesive and reservoir matrices is different and the Celgard ® layer is saturated with mineral oil; on standing the systems will equilibrate as a result of the transfer of mineral oil from the composition having a higher MO/PIB ratio to the lower. There will, however, be no significant transfer of drug since both the adhesive and reservoir layers are above saturation and the excess undissolved drug in the matrices is not readily susceptible to mass transfer. Therefore, on standing, the overall value of MO/PIB of the delivery system will be intermediate that of the initial MO/PIB ratios, the exact value of which will depend upon the relative amounts of the materials used in each of the reservoir and adhesive layers, as well as the amount of mineral oil which is in the Celgard membrane, and, of course, the time and temperature of storage.

In the following descriptions the compositions are defined in weight % of the matrix gels, disregarding structural elements of the TTS such as the backing members, release liners and rate control membranes.

EXAMPLE 1

A contact adhesive composition according to the prior art was fabricated from 47% MO, 27.8% LMW PIB, 22.2% HMW PIB (MO/PIB=0.94) and 3% clonidine. A drug reservoir composition according to the prior art was fabricated containing 47% MO, 22.2% LMW PIB, 17.8% HMW PIB (MO/PIB=1.18) and approximately 13% clonidine. Clonidine transdermal systems were fabricated from these materials as described above and the systems exhibited an apparent viscosity at 40° C. of approximately $8 \times 10^6$ poise.

EXAMPLE 2

Figure 2:
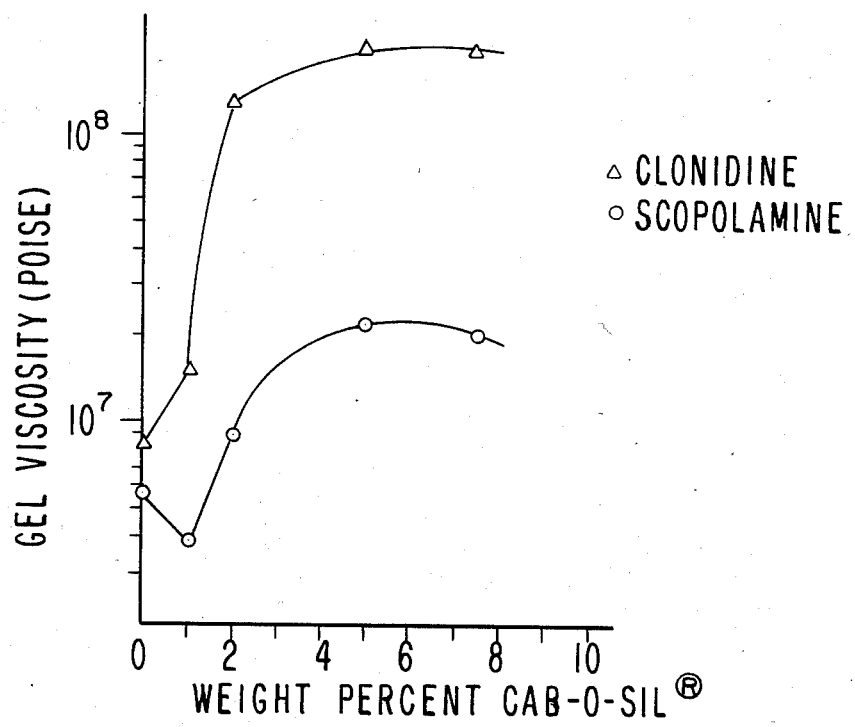
FIG. 2 is a graph showing the relationship between the CSD content of MO-PIB gels and the viscosity of clonidine and scopolamine compositions.

Since the Clonidine TTS of Example 1 exhibited low viscosity, systems were prepared from a series of adhesive and reservoir compositions corresponding to the compositions of Example 1 but with 1%, 2%, 5% and 7.5% CSD added at the expense of all other ingredients. The effect of the addition of CSD on apparent viscosity of the TTS is shown in FIG. 2.

EXAMPLE 3

Contact adhesive and reservoir compositions containing scopolamine according to the prior art were fabricated from respectively, 46.1% MO, 28.9% low molecular weight PIB, 23.0% high molecular weight PIB and 2.0% scopolamine and 41.7% MO, 26.2% LMW PIB, 20.8% HMW PIB and 11.3% scopolamine. A series of adhesive and reservoir compositions corresponding to the above but having 1%, 2%, 5% and 7.5% CSD added at the expense of all other ingredients was also prepared. The effect of CSD concentration on apparent viscosity of scopolamine transdermal system is also shown in FIG. 2.

EXAMPLE 4

Figure 3:
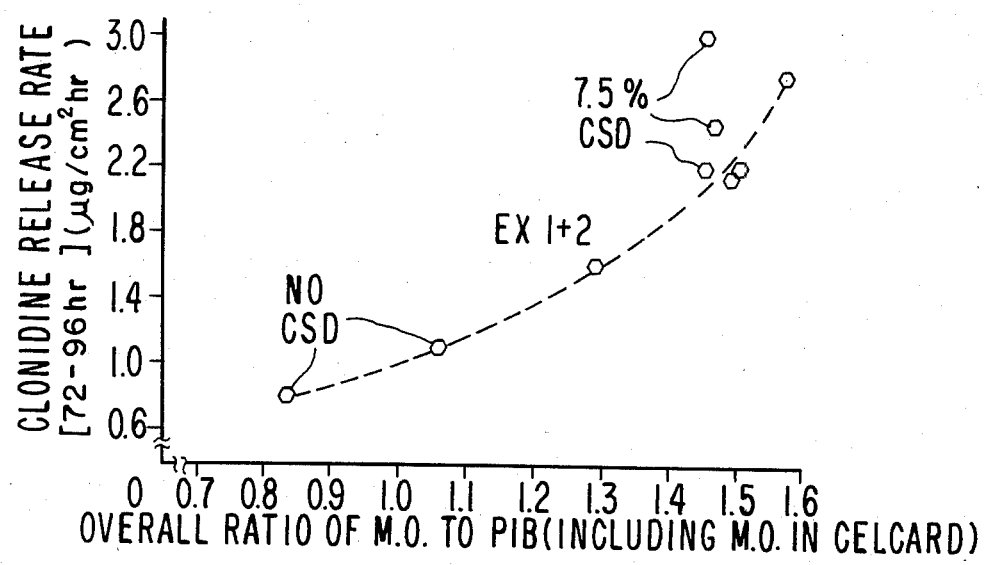
FIG. 3 is a graph showing the relationship between MO/PIB and in vitro clonidine release rates.

Contact adhesive and reservoir compositions at varying MO/PIB ratios without CSD, with 7.5% CSD added at the expense of the PIB fraction of Example 1 and with 7.5% CSD added at the expense of all other ingredients of Example 1 were made and formed into transdermal systems. By adding the CSD at the expense of the PIB it was possible to increase the value of MO/PIB as can be seen from Table I, below. The effect of the variation in MO/PIB (including MO in the Celgard layer) on the clonidine release rates from the transdermal systems fabricated from these compositions is shown in FIG. 3. As can be seen from FIG. 3 the higher MO/PIB values obtainable by adding the CSD at the expense of the PIB fraction produce release rates significantly higher than had heretofore been obtained.

Table I summarizes other data obtained on systems manufactured according to Examples 1, 2 and 4.

TABLE I

TTS (clonidine) System Comparison

| Attribute | Example 1 (No CSD) | Example 2 7.5% CSD (Expense of All) | Example 4 7.5% CSD (Expense of PIB) |
| --- | --- | --- | --- |
| Wt % clonidine in Drug Reservoir (D.R.) | 13.0 | 12.0 | 13.0 |
| Wt % clonidine in Contact Adhesive (C.A.) | 3.0 | 2.8 | 3.0 |
| Wt % mineral oil in C.A. and D.R. | 47.0 | 43.5 | 47.0 |
| MO/PIB Ratio in D.R. | 1.18 | 1.18 | 1.45 |
| MO/PIB Ratio in C.A. | 0.94 | 0.94 | 1.11 |
| MO/PIB Ratio Overall | | | |
| (incl. MO in Celgard) | 1.28 | 1.28 | 1.45 |
| (excl. MO in Celgard) | 1.06 | 1.06 | 1.28 |
| Prime Coat Thickness (microns) | 7.5 | 7.5 | 7.5 |
| DCs (µg/cm sec) | $2 \times 10^{-5}$ | $2 \times 10^{-5}$ | $1.2 \times 10^{-4}$ |
| Release Rate in vitro @ 32° C. (µg/cm² · hr) | 1.6 | 1.6 | 2.4 |
| Apparent Gel Viscosity (Poise) (0-24 hr creep) | $1.73 \times 10^6$ | $2.50 \times 10^8$ | $1.35 \times 10^8$ |
| System Backing/ Drug Reservoir Adhesion (g/cm) | 60 | 79 ± 12 | 69 ± 7 |

As shown in Table I the products produced by Examples 2 and 4 both exhibited an improvement in viscosity of approximately two orders of magnitude from the product of Example 1. The product of Example 4, however, also exhibited an order of magnitude improvement in drug release rate from the product of Example B 2 with no significant decrease in viscosity resulting from the elimination of a portion of the PIB used as a thickener.

EXAMPLE 5

Transdermal systems for dispensing clonidine and scopolamine were manufactured as described above from selected reservoir and adhesive composition described in Examples 1–4 and were subjected to package integrity testing. In this test the systems are packaged in sealed foil pouches and allowed to stand at ambient conditions for a minimum of 1 month until equilibrium conditions are approached. During this storage time the systems are vulnerable to cold flow of the adhesive and reservoir layers from their exposed edges which can impair removal from the pouch. Thereafter, the pouches are opened in the normally intended manner and the damage, if any, sustained by the TTS upon opening is observed. The possible conditions observed after opening the pouch with the casualness of the ordinary consumer, turning it upside down and shaking are:

(a) the TTS falls freely from the pouch;

(b) The TTS adheres to the pouch at its top side (side opposite the release liner) and peeling up on the release liner in an attempt to free the TTS from the pouch results in either:

(1) the intact TTS separating from the pouch in usable form or (2) the release liner coming off with the top side still adhering to the pouch, an unusable condition;

(c) the TTS adhering to the pouch at its release liner side and peeling up on the release liner allows removal of the intact TTS from the pouch or;

(d) the release liner adheres to one side of the pouch and the top adheres to the other side of the pouch causing irrepairable damage to the TTS on opening of the pouch.

Figure 4:
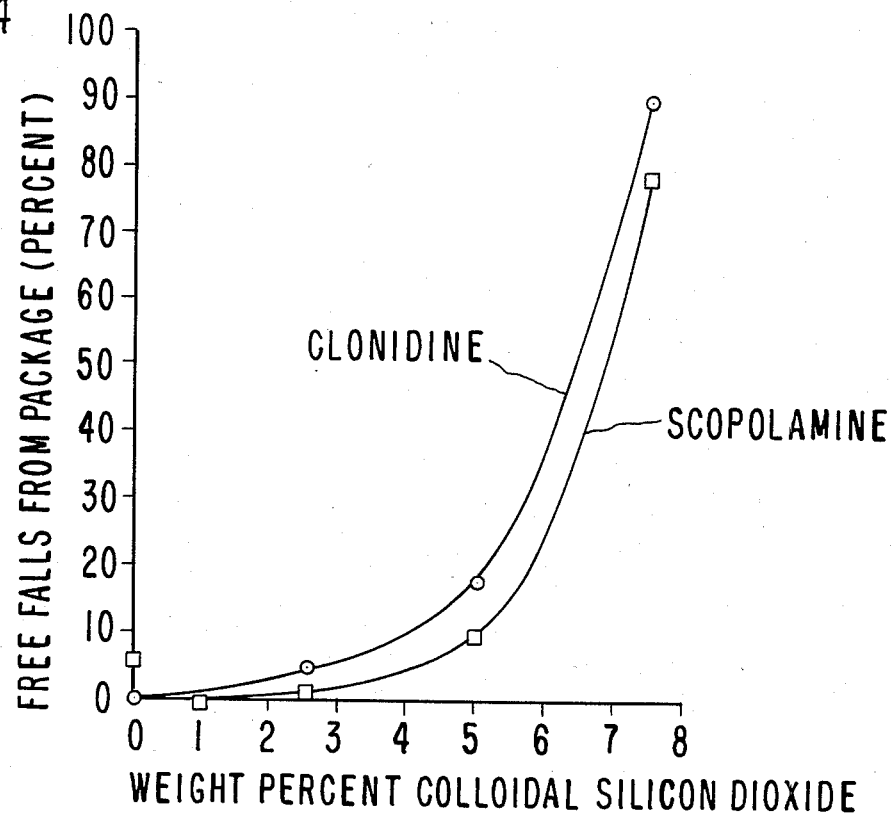
FIG. 4 is a graph showing the effect of CSD content on release of packaged transdermal systems.

FIG. 4 shows the composite results of this test on a large number of clonidine and scopolamine systems.

As can be seen, the incidence of failure was significantly reduced at CSD concentrations greater than 5%, equivalent to a viscosity of at least $1.5 \times 10^7$ poise (see FIG. 2).

EXAMPLE 6

Figure 5:
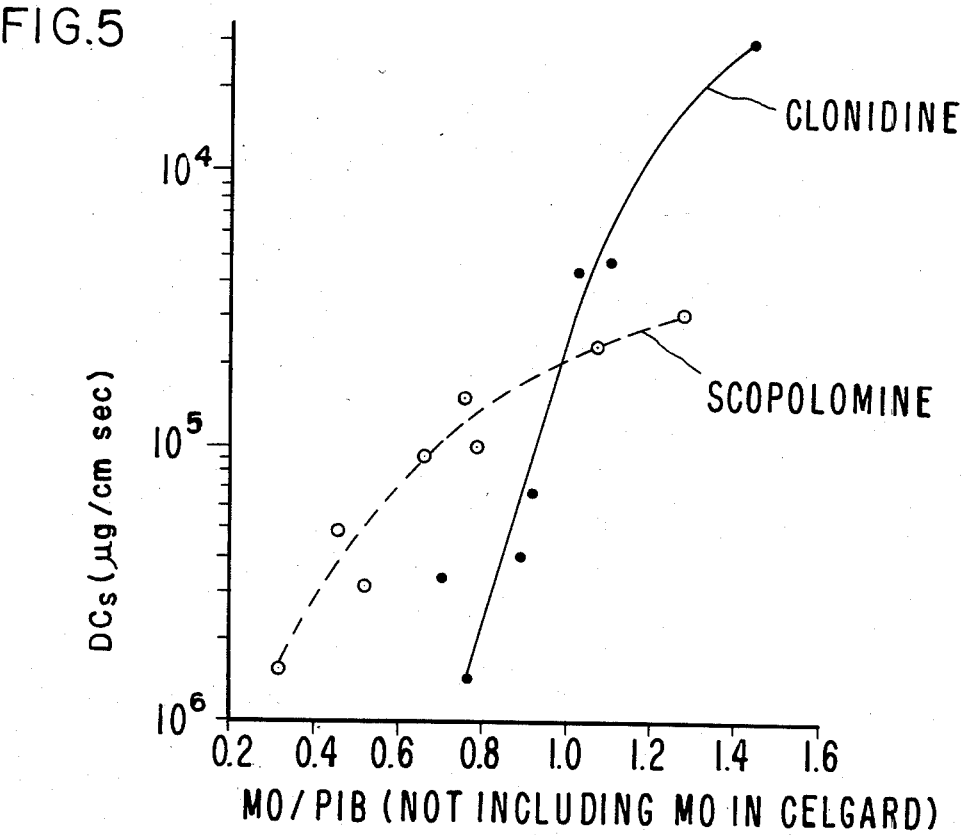
FIG. 5 is a graph showing the relationship between MO/PIB and permeability to clonidine and scopolamine.

A series of MO-PIB compositions at varying MO/PIB ratios were prepared and the permeability of the compositions to clonidine and scopolamine were determined. The results are shown in FIG. 5. As can be seen significant improvements in permeability are obtained at higher MO/PIB values. With respect to clonidine, values of 1.2 or above provide permeabilities greater than $1 \times 10^{-4}$ μg/cm sec which permits system to be designed in which the rate controlling membrane provides the predominant control mechanism of release rate.

EXAMPLE 7

Propranolol base loaded MO-PIB matrices were prepared having varying CSD loadings and the effect of CSD on in vitro permeability determined. Table II shows the effect of addition of Cab-O-Sil in MO/PIB monolithic systems on the transport properties of propranolol base at various percentages.

TABLE II

|  | SAMPLE A | SAMPLE B | SAMPLE C |
|---|---|---|---|
| MO % | 36.4 | 35.2 | 34.0 |
| LMW PIB % | 41.1 | 39.8 | 38.5 |
| Propranolol % | 15 | 15 | 15 |
| CSD % | 7.5 | 10 | 12.5 |
| MO/PIB | 0.88 | 0.88 | 0.88 |
| $DC_s$ (μg/cm · sec) | $4.8 \times 10^{-5}$ | $6.6 \times 10^{-4}$ | $2.5 \times 10^{-4}$ |

DISCUSSION OF RESULTS

As seen from FIG. 2 the addition of CSD to MO-PIB systems increases the viscosity of the gels. At about 3% CSD adequate viscosity is obtained even for such fluid systems as scopolamine and the viscosity tends to peak at about 5% CSD. Further addition of CSD does not produce a proportional increase in viscosity. Thus it would be expected that no significant improvement in physical properties of transdermal systems manufacture therefrom could be obtained at higher CSD levels. Nevertheless the results of the package opening tests described in FIG. 4 show a significant improvement in free falls above 5% CSD. By merely raising the CSD content from 5% to 7.5% the percent of free falls increased from 17.5% to 90% for the clonidine systems and from 10% to 79% for the scopolamine systems.

Prior to this invention the maximum MO/PIB ratio obtainable in a MO-PIB composition having adequate viscosity for the purposes contemplated herein was approximately 1.00. As seen in FIG. 5 at this ratio the permeability to certain drugs such as clonidine is lower than desired. Since the PIB is the thickening agent in MO-PIB gels, one would expect that as the MO-PIB ratio in any given system is increased, the viscosity would decrease. Also one would expect that as the viscosity of the MO/PIB gel increases as a result of the addition of CSD the drug permeability in the gel at a constant MO/PIB ratio would decrease. However, as can be seen from Table I, adding the CSD at the expense of the PIB fraction produces no significant reduction in viscosity from that obtained by adding the CSD at the expense of all the ingredients. Also as shown by Table II the permeability of MO-PIB matrix actually increases, (at a constant MO/PIB ratio) with the addition of up to about 10% CSD.

According to this invention therefore we provide MO-PIB-CSD mixtures having no less than about 6% CSD (on a drug-free basis) and preferably from 6-11% which have an extremely good combination of properties for use as matrices for dispensing a wide variety of moderately mineral oil soluble drugs. Further when these compositions are fabricated with MO/PIB ratios greater than about 1.0 drug permeabilities heretofore unobtainable are realized. In addition compositions according to this invention having MO/PIB ratios greater than about 1.2 can be used to to produce clonidine loaded matrices having clonidine permeabilities heretofore unobtainable. When used in fabricating laminated TTS's in which the microporous rate controlling membrane is saturated with MO the overall MO/PIB of the system can actually exceed about 1.45 while retaining desirable structural characteristics.

Having thus generally described our invention it will be apparent that various modifications can be made by workers skilled in the art without departing from the scope of this invention which is limited only by the following claims.

We claim:

1. A composition of matter suitable for use as a matrix in a drug delivery system comprising mineral oil, polyisobutylene, a moderately mineral oil soluble drug and at least 6% colloidal silicon dioxide, the MO/PIB ratio being at least 1.0, and being characterized by having a viscosity of at least $1.5 \times 10^7$ poise.

2. The composition of claim 1 wherein said moderately mineral oil soluble drug is dispersed therethrough in amounts up to about 40%.

3. The composition of claim 2 wherein said drug is present at a level between the saturation concentration of said drug in the composition and about 20%.

4. The composition of claim 3 wherein the ratio of mineral oil to polyisobutylene is at least 1.2 and the composition contains at least 7.5% by weight colloidal silicon dioxide.

5. The composition of claim 4 wherein said drug is selected from the group consisting of clonidine, scopolamine, propranolol, estradiol, phenylpropanolamine, ouabain, salbutamol, guanabenz, labetolol, atropine, haloperidol, bromocryptine, chlorpheniramine, metrifonate, isosorbide dinitrate and nitroglycerin.

6. The composition of claim 1 wherein said drug is clonidine and the permeability of the composition to clonidine is at least $1.0 \times 10^{-4}$ μg/cm sec.

7. The composition of claim 6 wherein the value of MO/PIB is at least 1.2.

8. In a transdermal therapeutic system, comprising a drug reservoir layer and an adhesive layer, a moderately mineral oil soluble drug dispersed in at least said reservoir layer at a concentration above the saturation concentration of said drug in said layer and a drug release rate release controlling membrane disposed between said reservoir and adhesive, said reservoir and said adhesive layer comprising a mixture of mineral oil and polyisobutylene, the improvement wherein said reservoir and said adhesive layer contain at least about 6% colloidal silicon dioxide, have a viscosity of at least $1.5 \times 10^7$ poise and and a ratio of mineral oil to polyisobutylene in the reservoir and adhesive of at least 1.2.

9. The transdermal therapeutic system of claim 8 wherein said release rate controlling membrane contains mineral oil and the overall ratio of MO/PIB in the transdermal therapeutic system is at least 1.4

10. The transdermal therapeutic system of claim 9 wherein said drug is selected from the group consisting of clonidine, scopolamine, propranolol, estradiol, phenylpropanolamine, ouabain, salbutamol, guanabenz, labetolol, atropine, haloperidol, bromocryptine, chlorpheniramine, metrifonate, isosorbide dinitrate and nitroglycerin.

11. The system of claim 9 wherein said drug is clonidine and the in vitro drug release rate from the system to an infinite sink is at least B 2.0 $\mu g/cm^2$ hr.

12. In a drug containing matrix composition consisting of a gel of mineral oil and polyisobutylene having a moderately mineral oil-soluble drug dispersed therethrough, the improvement wherein said composition has at least about 6.0% colloidal silicon dioxide dispersed therethrough, an MO/PIB ratio of at least 1.0 and a viscosity of at least about $1.5 \times 10^7$ poise.

13. The matrix composition of claim 11 wherein said MO/PIB ratio is at least about 1.2, the colloidal silicon dioxide is present in amounts of between 6 and 10% and said drug is present in an amount no less than saturation concentration and no greater than about 40%.

14. The composition of claim 12 wherein said drug is clonidine and the permeability of the matrix to clonidine is at least $1 \times 10^{-4}$ $\mu g/cm$ sec.

15. The composition of claim 1 wherein said polyisobutylene has an average molecular weight in the range of about 35,000 to about 1,500,000.

16. The composition of claim 5 wherein said polyisobutylene has an average molecular weight in the range of about 35,000 to 1,500,000.

17. The composition of claim 7 wherein said polyisobutylene has an average molecular weight in the range of about 35,000 to 1,500,000.

18. The composition of claim 13 wherein said polyisobutylene has an average molecular weight in the range of about 35,000 to 1,500,000.

* * * * *